United States Patent [19]

Bundy

[11] 4,128,712
[45] Dec. 5, 1978

[54] 9-DEOXY-9-METHYLENE-PGF$_1$-MORPHOLINYLAMIDES

[75] Inventor: Gordon L. Bundy, Portage, Mich.

[73] Assignee: The Upjohn Company, Kalamazoo, Mich.

[21] Appl. No.: 894,215

[22] Filed: Apr. 7, 1978

Related U.S. Application Data

[63] Continuation-in-part of Ser. No. 786,250, Apr. 11, 1977, Pat. No. 4,098,805, Continuation-in-part of Ser. No. 786,250, Apr. 11, 1977, Pat. No. 4,098,805.

[51] Int. Cl.$^2$ ............................................ C07C 177/00
[52] U.S. Cl. .................................... 542/426; 544/172; 544/176
[58] Field of Search ................ 542/426, 429; 544/172, 544/176

[56] References Cited
PUBLICATIONS

Derwent Abstract 16389U.B. NL 7211860-Q, May 3, 1973.
Derwent Abstract 75530x/40 U.S. 3981868, Sep. 21, 1976.

Primary Examiner—Paul J. Killos
Attorney, Agent, or Firm—Robert A. Armitage

[57] ABSTRACT

The present invention relates to novel 9-deoxy-9-methylene-PGF$_1$-morpholinylamides. These compounds are useful pharmacological agents, and are useful for the same purposes as the corresponding 9-deoxy-9-methylene-PGF-type acids.

32 Claims, No Drawings

9-DEOXY-9-METHYLENE-PGF$_1$-MORPHOLINYLAMIDES

CROSS REFERENCE TO RELATED APPLICATIONS

This application is a continuation-in-part of Ser. No. 786,250, filed Apr. 11, 1977, now U.S. Pat. No. 4,098,805, issued July 4, 1978.

The present invention relates to novel 9-deoxy-9-methylene-PGF$_1$-morpholinylamides, the essential material constituting a disclosure of which is incorporated here by reference from U.S. Pat. No. 4,098,805.

I claim:

1. A prostaglandin analog of the formula

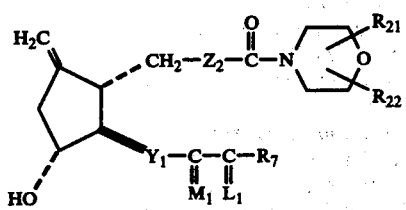

wherein Y$_1$ is trans—CH=CH—, —C≡C—, or —CH$_2$CH$_2$— wherein M$_1$ is wherein M$_1$ is

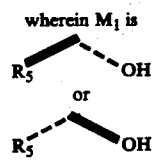

wherein R$_5$ is hydrogen or methyl;

wherein L$_1$ is

or a mixture of

and

wherein R$_3$ and R$_4$ are hydrogen, methyl, or fluoro, being the same or different, with the proviso that one of R$_3$ and R$_4$ is fluoro only when the other is hydrogen or fluoro;

wherein Z$_2$ is
(1) —(CH$_2$)$_3$—(CH$_2$)$_g$—CH$_2$—,
(2) —(CH$_2$)$_3$—(CH$_2$)$_g$—CF$_2$—,
(3) —CH$_2$—O—CH$_2$—(CH$_2$)$_g$—CH$_2$—,
(4) —C≡C—CH$_2$—(CH$_2$)$_g$—CH$_2$—,
(5) —CH$_2$—C≡C—(CH$_2$)$_g$—CH$_2$—, (6) 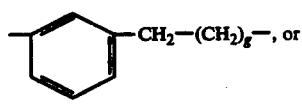 or

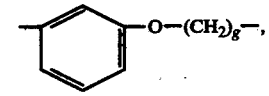

wherein g is one, 2 or 3;
wherein R$_7$ is
(1) —(CH$_2$)$_m$—CH$_3$,

 , or

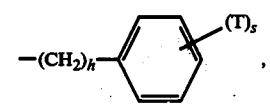

wherein m is one to 5, inclusive, h is zero or one, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that R$_7$ is

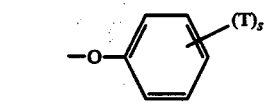

wherein T and s are as defined above, only when R$_3$ and R$_4$ are hydrogen or methyl, being the same or different; and wherein R$_{21}$ and R$_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive.

2. A prostaglandin analog according to claim 1, wherein Y$_1$ is —C≡C—.

3. 9-Deoxy-9-methylene-13,14-didehydro-PGF$_1$, morpholinylamide, a prostaglandin analog according to claim 2.

4. A prostaglandin analog according to claim 1, wherein Y$_1$ is —CH$_2$CH$_2$—.

5. 9-Deoxy-9-methylene-13,14-dihydro-PGF$_1$, morpholinylamide, a prostaglandin analog according to claim 4.

6. A prostaglandin analog according to claim 1, wherein Y$_1$ is trans—CH=CH—.

7. A prostaglandin analog according to claim 6, wherein Z$_2$ is aromatic.

8. 9-Deoxy-9-methylene-3,7-inter-m-phenylene-3-oxa-4,5,6-trinor-PGF$_1$, morpholinylamide, a prostaglandin analog according to claim 7.

9. 9-Deoxy-9-methylene-3,7-inter-m-phenylene-4,5,6-trinor-PGF$_1$, morpholinylamide a prostaglandin analog according to claim 7.

10. A prostaglandin analog according to claim 6, wherein Z$_2$ is aliphatic.

11. A prostaglandin analog according to claim 10, wherein $M_1$ is

12. 15-epi-9-deoxy-9-methylene-$PGF_1$, morpholinylamide, a prostaglandin analog according to claim 11.

13. A prostaglandin analog according to claim 10, wherein $M_1$ is

14. A prostaglandin analog according to claim 13, wherein $Z_2$ is cis—CH=CH—$CH_2$—$(CH_2)_g$—$CH_2$—.

15. A prostaglandin analog according to claim 14, wherein $R_7$ is

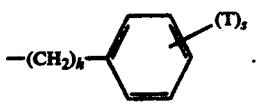

16. 9-Deoxy-9-methylene-17-phenyl-18,19,20-trinor-$PGF_1$, morpholinylamide, a prostaglandin analog according to claim 15.

17. A prostaglandin analog according to claim 14, wherein $R_7$ is

18. 9-Deoxy-9-methylene-16-phenoxy-17,18,19,20-tetranor-$PGF_1$, morpholinylamide, a prostaglandin analog according to claim 17.

19. A prostaglandin analog according to claim 14, wherein $R_7$ is —$(CH_2)_m$—$CH_3$.

20. A prostaglandin analog according to claim 19, wherein m is 3.

21. A prostaglandin analog according to claim 20, wherein g is 3.

22. 2a,2b-Dihomo-9-deoxy-9-methylene-15-methyl-$PGF_1$, morpholinylamide, a prostaglandin analog according to claim 21.

23. A prostaglandin analog according to claim 20, wherein g is one.

24. A prostaglandin analog according to claim 23, wherein at least one of $R_3$ and $R_4$ is methyl.

25. 9-Deoxy-9-methylene-16,16-dimethyl-$PGF_1$, morpholinylamide, a prostaglandin analog according to claim 24.

26. A prostaglandin analog according to claim 23, wherein at least one of $R_3$ and $R_4$ is fluoro.

27. 9-Deoxy-9-methylene-16,16-difluoro-$PGF_1$, morpholinylamide, a prostaglandin analog according to claim 26.

28. A prostaglandin analog according to claim 23, wherein $R_3$ and $R_4$ are both hydrogen.

29. A prostaglandin analog according to claim 28, wherein $R_5$ is methyl.

30. 9-Deoxy-9-methylene-15-methyl-$PGF_1$, morpholinyl- a prostaglandin analog according to claim 29.

31. A prostaglandin analog according to claim 28, wherein $R_5$ is hydrogen.

32. 9-Deoxy-9-methylene-$PGF_1$, morpholinylamide, a prostaglandin analog according to claim 31.

* * * * *

UNITED STATES PATENT OFFICE
CERTIFICATE OF CORRECTION

Patent No. 4,128,712     Dated December 5, 1978

Inventor(s) Gordon L. Bundy

It is certified that error appears in the above-identified patent and that said Letters Patent are hereby corrected as shown below:

Column 4, lines 35-36, "$PGF_1$, morpholinyl-" should read -- $PGF_1$, morpholinylamide --.

*Signed and Sealed this*

*Seventeenth* Day of *July 1979*

[SEAL]

Attest:

LUTRELLE F. PARKER

*Attesting Officer*     *Acting Commissioner of Patents and Trademarks*